(12) United States Patent
Liu et al.

(10) Patent No.: US 12,415,016 B2
(45) Date of Patent: Sep. 16, 2025

(54) PREPARATION METHOD FOR SILK FIBROIN NERVE GRAFT FUSED WITH NT3

(71) Applicant: NANTONG UNIVERSITY, Jiangsu (CN)

(72) Inventors: Yan Liu, Jiangsu (CN); Mei Liu, Jiangsu (CN); Xiaosong Gu, Jiangsu (CN); Tuchen Guan, Jiangsu (CN)

(73) Assignee: NANTONG UNIVERSITY (CN)

( * ) Notice: Subject to any disclaimer, the term of this patent is extended or adjusted under 35 U.S.C. 154(b) by 0 days.

(21) Appl. No.: 17/633,950

(22) PCT Filed: Jul. 24, 2020

(86) PCT No.: PCT/CN2020/104048
§ 371 (c)(1),
(2) Date: Feb. 8, 2022

(87) PCT Pub. No.: WO2021/227255
PCT Pub. Date: Nov. 18, 2021

(65) Prior Publication Data
US 2023/0144643 A1 May 11, 2023

(30) Foreign Application Priority Data
May 12, 2020 (CN) .......................... 202010396807.7

(51) Int. Cl.
*A61L 27/22* (2006.01)
*C07K 14/48* (2006.01)
*C12N 15/62* (2006.01)

(52) U.S. Cl.
CPC ............ *A61L 27/227* (2013.01); *C07K 14/48* (2013.01); *C12N 15/62* (2013.01); *A61L 2430/32* (2013.01)

(58) Field of Classification Search
CPC .......................... C07K 2319/00; C12N 15/62
See application file for complete search history.

(56) References Cited

FOREIGN PATENT DOCUMENTS

| CN | 103705979 | * | 4/2014 | ............. A61L 27/36 |
| CN | 108114315 | * | 6/2018 | ............ A61L 27/383 |

OTHER PUBLICATIONS

Hopkins et al. "Silk Hydrogels as Soft Substrates for Neural Tissue Engineering" Adv. Funct. Mater. 2013, 23, 5140-5149 (Year: 2013).*
English Translation for CN103705979, Google Patents, 10 pages, Accessed Jul. 28, 2025 (Year: 2025).*
English Translation for CN108114315, Google Patents, 6 pages, Accessed Jul. 28, 2025 (Year: 2025).*

* cited by examiner

*Primary Examiner* — Thane Underdahl (57) ABSTRACT

A silk fibroin nerve graft fused with NT3 and a preparation method therefor is provided. The method includes the steps of: synthesizing a gene fragment containing a silk fibroin light chain and NT-3, connecting the fragment to a pET-30 expression vector, and transferring the obtained recombinant expression vector into BL21 *Escherichia coli* to obtain a fusion protein; placing a silk fibroin fiber web in a mold, mixing the fusion protein and a silk fibroin solution, and performing freeze drying to enable the silk fibroin to be crosslinked with the fusion protein to form a nerve conduit; and after deformation processing, finally obtaining a silk fibroin nerve graft having NT-3 activity. The silk fibroin nerve graft can provide a mechanical support, exert nerve protection and nerve regeneration promotion functions in a long term, and adjust the proportion of NT-3 bioactive peptides in the nerve conduit, facilitating repair of nerve injuries.

11 Claims, 2 Drawing Sheets
Specification includes a Sequence Listing.

SEQUENCE LISTING

```
<160> NUMBER OF SEQ ID NOS: 4

<210> SEQ ID NO 1
<211> LENGTH: 253
<212> TYPE: PRT
<213> ORGANISM: Artificial Sequence
<220> FEATURE:
<223> OTHER INFORMATION: PEPTIDE, silk fibroin

<400> SEQUENCE: 1

Met His His His His His His Ala Pro Ser Val Thr Ile Asn Gln Tyr
1               5                   10                  15

Ser Asp Asn Glu Ile Pro Arg Asp Ile Asp Asp Gly Lys Ala Ser Ser
            20                  25                  30

Val Ile Ser Arg Ala Trp Asp Tyr Val Asp Asp Thr Asp Lys Ser Ile
        35                  40                  45

Ala Ile Leu Asn Val Gln Glu Ile Leu Lys Asp Met Ala Ser Gln Gly
    50                  55                  60

Asp Tyr Ala Ser Gln Ala Ser Ala Val Ala Gln Thr Ala Gly Ile Ile
65                  70                  75                  80

Ala His Leu Ser Ala Gly Ile Pro Gly Asp Ala Cys Ala Ala Ala Asn
                85                  90                  95

Val Ile Asn Ser Tyr Thr Asp Gly Val Arg Ser Gly Asn Phe Ala Gly
            100                 105                 110

Phe Arg Gln Ser Leu Gly Pro Phe Phe Gly His Val Gly Gln Asn Leu
        115                 120                 125

Asn Leu Ile Asn Gln Leu Val Ile Asn Pro Gly Gln Leu Arg Tyr Ser
    130                 135                 140

Val Gly Pro Ala Leu Gly Cys Ala Gly Gly Gly Arg Ile Tyr Asp Phe
145                 150                 155                 160

Glu Ala Ala Trp Asp Ala Ile Leu Ala Ser Ser Asp Ser Ser Phe Leu
                165                 170                 175
```

Asn Glu Glu Tyr Cys Ile Val Lys Arg Leu Tyr Asn Ser Arg Asn Ser
            180                 185                 190

Gln Ser Asn Asn Ile Ala Ala Tyr Ile Thr Ala His Leu Leu Pro Pro
        195                 200                 205

Val Ala Gln Val Phe His Gln Ser Ala Gly Ser Ile Thr Asp Leu Leu
    210                 215                 220

Arg Gly Val Gly Asn Gly Asn Asp Ala Thr Gly Leu Val Ala Asn Ala
225                 230                 235                 240

Gln Arg Tyr Ile Ala Gln Ala Ala Ser Gln Val His Val
                245                 250

<210> SEQ ID NO 2
<211> LENGTH: 372
<212> TYPE: PRT
<213> ORGANISM: Artificial Sequence
<220> FEATURE:
<223> OTHER INFORMATION: PEPTIDE, silk fibroin fused with NT3

<400> SEQUENCE: 2

Met His His His His His Ala Pro Ser Val Thr Ile Asn Gln Tyr
1               5                   10                  15

Ser Asp Asn Glu Ile Pro Arg Asp Ile Asp Asp Gly Lys Ala Ser Ser
            20                  25                  30

Val Ile Ser Arg Ala Trp Asp Tyr Val Asp Thr Asp Lys Ser Ile
        35                  40                  45

Ala Ile Leu Asn Val Gln Glu Ile Leu Lys Asp Met Ala Ser Gln Gly
    50                  55                  60

Asp Tyr Ala Ser Gln Ala Ser Ala Val Ala Gln Thr Ala Gly Ile Ile
65                  70                  75                  80

Ala His Leu Ser Ala Gly Ile Pro Gly Asp Ala Cys Ala Ala Ala Asn
                85                  90                  95

Val Ile Asn Ser Tyr Thr Asp Gly Val Arg Ser Gly Asn Phe Ala Gly
            100                 105                 110

Phe Arg Gln Ser Leu Gly Pro Phe Phe Gly His Val Gly Gln Asn Leu
        115                 120                 125

Asn Leu Ile Asn Gln Leu Val Ile Asn Pro Gly Gln Leu Arg Tyr Ser
    130                 135                 140

Val Gly Pro Ala Leu Gly Cys Ala Gly Gly Arg Ile Tyr Asp Phe
145                 150                 155                 160

Glu Ala Ala Trp Asp Ala Ile Leu Ala Ser Ser Asp Ser Ser Phe Leu
                165                 170                 175

Asn Glu Glu Tyr Cys Ile Val Lys Arg Leu Tyr Asn Ser Arg Asn Ser
            180                 185                 190

Gln Ser Asn Asn Ile Ala Ala Tyr Ile Thr Ala His Leu Leu Pro Pro
        195                 200                 205

Val Ala Gln Val Phe His Gln Ser Ala Gly Ser Ile Thr Asp Leu Leu
    210                 215                 220

Arg Gly Val Gly Asn Gly Asn Asp Ala Thr Gly Leu Val Ala Asn Ala
225                 230                 235                 240

Gln Arg Tyr Ile Ala Gln Ala Ala Ser Gln Val His Val Tyr Ala Glu
                245                 250                 255

His Lys Ser His Arg Gly Glu Tyr Ser Val Cys Asp Ser Glu Ser Leu
            260                 265                 270

Trp Val Thr Asp Lys Ser Ser Ala Ile Asp Ile Arg Gly His Gln Val
        275                 280                 285

```
Thr Val Leu Gly Glu Ile Lys Thr Gly Asn Ser Pro Val Lys Gln Tyr
    290                 295                 300

Phe Tyr Glu Thr Arg Cys Lys Glu Ala Arg Pro Val Lys Asn Gly Cys
305                 310                 315                 320

Arg Gly Ile Asp Asp Lys His Trp Asn Ser Gln Cys Lys Thr Ser Gln
                325                 330                 335

Thr Tyr Val Arg Ala Leu Thr Ser Glu Asn Asn Lys Leu Val Gly Trp
            340                 345                 350

Arg Trp Ile Arg Ile Asp Thr Ser Cys Val Cys Ala Leu Ser Arg Lys
                355                 360                 365

Ile Gly Arg Thr
    370

<210> SEQ ID NO 3
<211> LENGTH: 382
<212> TYPE: PRT
<213> ORGANISM: Artificial Sequence
<220> FEATURE:
<223> OTHER INFORMATION: PEPTIDE, silk fibroin fused with NT3

<400> SEQUENCE: 3

Met His His His His His Ala Pro Ser Val Thr Ile Asn Gln Tyr
1               5                   10                  15

Ser Asp Asn Glu Ile Pro Arg Asp Ile Asp Asp Gly Lys Ala Ser Ser
                20                  25                  30

Val Ile Ser Arg Ala Trp Asp Tyr Val Asp Thr Asp Lys Ser Ile
            35                  40                  45

Ala Ile Leu Asn Val Gln Glu Ile Leu Lys Asp Met Ala Ser Gln Gly
    50                  55                  60

Asp Tyr Ala Ser Gln Ala Ser Val Ala Gln Thr Ala Gly Ile Ile
65                  70                  75                  80

Ala His Leu Ser Ala Gly Ile Pro Gly Asp Ala Cys Ala Ala Asn
                85                  90                  95

Val Ile Asn Ser Tyr Thr Asp Gly Val Arg Ser Gly Asn Phe Ala Gly
                100                 105                 110

Phe Arg Gln Ser Leu Gly Pro Phe Phe Gly His Val Gly Gln Asn Leu
            115                 120                 125

Asn Leu Ile Asn Gln Leu Val Ile Asn Pro Gly Gln Leu Arg Tyr Ser
    130                 135                 140

Val Gly Pro Ala Leu Gly Cys Ala Gly Gly Arg Ile Tyr Asp Phe
145                 150                 155                 160

Glu Ala Ala Trp Asp Ala Ile Leu Ala Ser Ser Asp Ser Ser Phe Leu
                165                 170                 175

Asn Glu Glu Tyr Cys Ile Val Lys Arg Leu Tyr Asn Ser Arg Asn Ser
            180                 185                 190

Gln Ser Asn Asn Ile Ala Ala Tyr Ile Thr Ala His Leu Leu Pro Pro
    195                 200                 205

Val Ala Gln Val Phe His Gln Ser Ala Gly Ser Ile Thr Asp Leu Leu
210                 215                 220

Arg Gly Val Gly Asn Gly Asn Asp Ala Thr Gly Leu Val Ala Asn Ala
225                 230                 235                 240

Gln Arg Tyr Ile Ala Gln Ala Ala Ser Gln Val His Val Gly Gly Gly
                245                 250                 255

Gly Ser Gly Gly Gly Gly Ser Tyr Ala Glu His Lys Ser His Arg Gly
            260                 265                 270
```

```
Glu Tyr Ser Val Cys Asp Ser Glu Ser Leu Trp Val Thr Asp Lys Ser
            275                 280                 285

Ser Ala Ile Asp Ile Arg Gly His Gln Val Thr Val Leu Gly Glu Ile
        290                 295                 300

Lys Thr Gly Asn Ser Pro Val Lys Gln Tyr Phe Tyr Glu Thr Arg Cys
305                 310                 315                 320

Lys Glu Ala Arg Pro Val Lys Asn Gly Cys Arg Gly Ile Asp Asp Lys
                325                 330                 335

His Trp Asn Ser Gln Cys Lys Thr Ser Gln Thr Tyr Val Arg Ala Leu
            340                 345                 350

Thr Ser Glu Asn Asn Lys Leu Val Gly Trp Arg Trp Ile Arg Ile Asp
        355                 360                 365

Thr Ser Cys Val Cys Ala Leu Ser Arg Lys Ile Gly Arg Thr
370                 375                 380

<210> SEQ ID NO 4
<211> LENGTH: 501
<212> TYPE: PRT
<213> ORGANISM: Artificial Sequence
<220> FEATURE:
<223> OTHER INFORMATION: PEPTIDE, silk fibroin fused with NT3

<400> SEQUENCE: 4

Met His His His His His His Ala Pro Ser Val Thr Ile Asn Gln Tyr
1               5                   10                  15

Ser Asp Asn Glu Ile Pro Arg Asp Ile Asp Asp Gly Lys Ala Ser Ser
            20                  25                  30

Val Ile Ser Arg Ala Trp Asp Tyr Val Asp Asp Thr Asp Lys Ser Ile
        35                  40                  45

Ala Ile Leu Asn Val Gln Glu Ile Leu Lys Asp Met Ala Ser Gln Gly
    50                  55                  60

Asp Tyr Ala Ser Gln Ala Ser Ala Val Ala Gln Thr Ala Gly Ile Ile
65                  70                  75                  80

Ala His Leu Ser Ala Gly Ile Pro Gly Asp Ala Cys Ala Ala Ala Asn
                85                  90                  95

Val Ile Asn Ser Tyr Thr Asp Gly Val Arg Ser Gly Asn Phe Ala Gly
            100                 105                 110

Phe Arg Gln Ser Leu Gly Pro Phe Phe Gly His Val Gly Gln Asn Leu
        115                 120                 125

Asn Leu Ile Asn Gln Leu Val Ile Asn Pro Gly Gln Leu Arg Tyr Ser
    130                 135                 140

Val Gly Pro Ala Leu Gly Cys Ala Gly Gly Arg Ile Tyr Asp Phe
145                 150                 155                 160

Glu Ala Ala Trp Asp Ala Ile Leu Ala Ser Ser Asp Ser Ser Phe Leu
                165                 170                 175

Asn Glu Glu Tyr Cys Ile Val Lys Arg Leu Tyr Asn Ser Arg Asn Ser
            180                 185                 190

Gln Ser Asn Asn Ile Ala Ala Tyr Ile Thr Ala His Leu Leu Pro Pro
        195                 200                 205

Val Ala Gln Val Phe His Gln Ser Ala Gly Ser Ile Thr Asp Leu Leu
    210                 215                 220

Arg Gly Val Gly Asn Gly Asn Asp Ala Thr Gly Leu Val Ala Asn Ala
225                 230                 235                 240

Gln Arg Tyr Ile Ala Gln Ala Ala Ser Gln Val His Val Tyr Ala Glu
                245                 250                 255
```

-continued

```
His Lys Ser His Arg Gly Glu Tyr Ser Val Cys Asp Ser Glu Ser Leu
            260                 265                 270

Trp Val Thr Asp Lys Ser Ser Ala Ile Asp Ile Arg Gly His Gln Val
        275                 280                 285

Thr Val Leu Gly Glu Ile Lys Thr Gly Asn Ser Pro Val Lys Gln Tyr
        290                 295                 300

Phe Tyr Glu Thr Arg Cys Lys Glu Ala Arg Pro Val Lys Asn Gly Cys
305                 310                 315                 320

Arg Gly Ile Asp Asp Lys His Trp Asn Ser Gln Cys Lys Thr Ser Gln
            325                 330                 335

Thr Tyr Val Arg Ala Leu Thr Ser Glu Asn Asn Lys Leu Val Gly Trp
            340                 345                 350

Arg Trp Ile Arg Ile Asp Thr Ser Cys Val Cys Ala Leu Ser Arg Lys
            355                 360                 365

Ile Gly Arg Thr Gly Gly Gly Ser Gly Gly Gly Gly Ser Tyr Ala
    370                 375                 380

Glu His Lys Ser His Arg Gly Glu Tyr Ser Val Cys Asp Ser Glu Ser
385                 390                 395                 400

Leu Trp Val Thr Asp Lys Ser Ser Ala Ile Asp Ile Arg Gly His Gln
                405                 410                 415

Val Thr Val Leu Gly Glu Ile Lys Thr Gly Asn Ser Pro Val Lys Gln
                420                 425                 430

Tyr Phe Tyr Glu Thr Arg Cys Lys Glu Ala Arg Pro Val Lys Asn Gly
            435                 440                 445

Cys Arg Gly Ile Asp Asp Lys His Trp Asn Ser Gln Cys Lys Thr Ser
    450                 455                 460

Gln Thr Tyr Val Arg Ala Leu Thr Ser Glu Asn Asn Lys Leu Val Gly
465                 470                 475                 480

Trp Arg Trp Ile Arg Ile Asp Thr Ser Cys Val Cys Ala Leu Ser Arg
                485                 490                 495

Lys Ile Gly Arg Thr
                500
```

PREPARATION METHOD FOR SILK FIBROIN NERVE GRAFT FUSED WITH NT3

This application contains Sequence Listing ASCII text file as a separate part of the disclosure, the name of the ASCII text file is "ZH202201_SEQUENCE LISTING", the date of creation of the ASCII text file is Dec. 15, 2022, and its size is 13644 bytes. The entire contents of the ASCII text file are hereby incorporated by reference.

FIELD

The present invention relates to the field of biomedical materials, and specifically relates to a silk fibroin nerve graft having NT3 activity, capable of promoting nerve recovery, and applicable to peripheral nerve, spinal cord injury and cerebral injury repair and regeneration.

BACKGROUND

Along with the development of emerging disciplines such as tissue engineering and biomaterials, more and more biomaterials are applied to nerve repair. Excellent biomaterials should have good biocompatibility, and support adhesion, migration, intercellular interaction, proliferation and differentiation of cells. Moreover, these materials also need to possess an appropriate degradation rate and mechanical properties and cause a limited immune response, and can be processed in multiple options. The structure and form of the materials can be modified according to specific needs of a tissue. Proteins are components of a natural tissue, and are rational choices in tissue engineering applications. Structural proteins such as collagen, elastin, elastin peptide, albumin and fibrin are used as suture lines, tissue scaffolds, haemostatic, and drug delivery agents.

Nerve injuries include peripheral nerve injuries and central nervous injuries. At preset, treatment on long-distance peripheral nerve injuries and spinal cord injuries requires application of different types of grafts in most cases, and due to lack of sources, a limited application scope and other shortcomings of autologous nerve grafts, xenografts or the like, people start to look for new tissue engineering graft substitutes. Silk fibroin is a common natural biopolymer material, and has a long history as suture lines for human bodies. In recent years, some characteristics of silk fibroin, as a biomaterial, gradually attract people's attention. Compared with other protein-based biomaterials of tissues of the homogenic or xenogenic origin, silk fibroin has several advantages: good biocompatibility, excellent mechanical properties, controllable biodegradability, a simple processing process, and the like. Moreover, silk fibroin polymers exhibit different processing plasticity. By means of changes in manufacturing technology, multiple matrix configurations can be implemented, including three-dimensional porous foam, nanofiber, aquagel, conduits and films, and multiple tissue repairs can be used. Neurotrophic factor 3 is a protein encoded by an NTF3 gene, is an essential member of a family of nerve growth factors, can nourish nerve cells of peripheral and central nervous systems, and not only facilitates survival of existing neurons, but also promotes survival and differentiation of new neurons and connection of synapses.

At present, the function of only using silk fibroin to construct a tissue engineering scaffold is relatively simple, and a nerve tissue recovery promoting function is relatively limited. In researches, nerve grafts are soaked in neurotrophic factors (e.g. NGF) or are mixed with silk fibroin and then freeze-dried to form a conduit, which has a good nerve growth promoting function, but this function may gradually become weak over time. Moreover, use of the nerve grafts is greatly restricted due to the instability of the neurotrophic factors in vivo and limited sources.

SUMMARY

With regard to the shortcomings of the prior art, the present invention relates to combining a bioactive peptide fragment of a neuroprotective factor 3 (NT-3) with a peptide fragment of a silk fibroin light chain to form a fusion protein, and using the fusion protein as a basis, performing self-assembly of silk fibroin to obtain a novel nerve graft capable of providing a good mechanical support and exerting a long-term stable nerve protection function.

The technical solution of the present invention is as follows.

A preparation method for a silk fibroin nerve graft fused with NT3 includes the following steps:

A gene fragment containing a silk fibroin light chain and NT-3 is synthesized, the fragment is connected to a pET-30 expression vector, and the obtained recombinant expression vector is transferred into BL21 *Escherichia coli* to obtain a fusion protein.

The fusion protein and a silk fibroin solution are mixed to obtain a mixed protein solution, a silk fibroin fiber web is placed in a mold, the mixed protein solution is poured in the mold, and freeze drying is performed to form a nerve conduit; and after deformation processing, a silk fibroin nerve graft having NT-3 activity is finally obtained. Furthermore, the silk fibroin fiber web is woven by a braider by using a silk fibroin fiber.

Furthermore, a preparation method for the silk fibroin solution is: placing a silk fibroin fiber into a lithium thiocyanate hydrate for dissolution, transferring the solution obtained after dissolution into a dialysis bag, and performing dialysis for 60 to 80 hours by using triple distilled water as a dialyzate to obtain the silk fibroin solution.

Furthermore, a preparation method for the silk fibroin fiber is: placing mulberry silk into a sodium carbonate solution, boiling for 20 minutes or more, taking out the mulberry silk, washing with triple distilled water, and repeating the steps two to four times to obtain the silk fibroin fiber, external sericin of which is removed.

Furthermore, the concentration of a fusion protein and silk fibroin solution is 5% to 40%, and the mass ratio of the fusion protein to the silk fibroin is 1:99 to 50:50.

Furthermore, the deformation processing is soaking in 60% ethanol for processing for 10 h to 14 h.

Furthermore, the molecular weight cut off of the dialysis bag is 12-16 kDa.

Furthermore, the temperature for freeze drying is −70° C.

Furthermore, the concentration of the lithium thiocyanate hydrate is 9 mol/L.

The present invention further provides a silk fibroin nerve graft fused with NT3, which is prepared by using the foregoing preparation method.

Beneficial Effects

The prior art mainly adopts a method of adsorption of neurotrophic factors or covalent linkage to scaffolds. The present invention uses a bioactive fragment of NT-3 and light chain silk fibroin to co-express a fusion protein, which is an effective component taking silk fibroin as the main body and fused with NT-3, and is capable of being secured in a silk fibroin conduit together with the silk fibroin. On the premise that components of the silk fibroin are not changed, the fusion protein can exert nerve protection and nerve regeneration promotion functions in a long term.

The main material used in the present invention is silk fibroin, assisted by a silk fibroin light chain fused with an NT-3 bioactive peptide fragment. In a processing process, no toxic substance or substance having side effects, such as a crosslinking agent or a surfactant, is added, and therefore, good biocompatibility is obtained.

When the silk fibroin fusion protein provided by the present invention is co-cultured with a nerve tissue cell in vitro, morphological observation and measurement on expression of NT-3 related factors both show an obvious growth promotion effect, where the activity of FIBL-NT3-L-NT3 is the strongest.

The silk fibroin light chain fused with the NT-3 functional peptide fragment is introduced to the silk fibroin conduit provided by the present invention before crystallization of the silk fibroin, and therefore, in a silk fibroin self-assembly process, an NT-3 bioactive polypeptide is secured in the silk fibroin conduit together with the silk fibroin light chain, providing a mechanical support, exerting nerve protection and nerve regeneration promotion functions in a long term, and adjusting the proportion of NT-3 bioactive peptides in the nerve conduit according to actual situations, facilitating repair of nerve injuries.

DETAILED DESCRIPTION

Embodiment 1

A preparation method for a silk fibroin nerve graft fused with NT3 includes the following steps:
1. Expression and purification of a silk fibroin fusion protein: a recombinant expression vector is constructed, and purification is performed after a target protein is expressed.
2. Obtaining of a silk fibroin fiber of silk: raw silk of mulberry silk is taken, sericin is removed, and the silk fibroin fiber of the mulberry silk is obtained.
3. Preparation of a silk fibroin solution.
4. Preparation of a silk fibroin fiber web.
5. The silk fibroin fiber web is placed in a mold, after the protein solutions obtained in steps 1 and 3 are mixed, the mixture is poured in the mold, and freeze drying is performed to enable the silk fibroin to undergo self-assembly to form a nerve conduit.

Embodiment 2

A preparation method for a silk fibroin nerve graft fused with NT3 includes the following steps:
1. Construction of a recombinant expression vector: synthesizing a gene fragment containing a silk fibroin light chain and NT-3 is synthesized, and the fragment is connected to a pET-30 expression vector to complete construction of the recombinant expression vector, where different fusion protein sequences having tags and linkers are shown as follows:

Fusion Protein Sequences (Having N-Terminus his and Flexible Linkers):

FIBL Protein Length = 253 MW = 26898.8 pI = 6.10
SEQ ID NO: 1
MHHHHHHAPSVTINQYSDNEIPRDIDDGKASSVISRAWDYVDDTKSIA

ILNVQEILKDMASQGDYASQASAVAQTAGIIAHLSAGIPGDACAAANVI

NSYTDGVRSGNFAGFRQSLGPFFGHVGQNLNLINQLVINPGQLRYSVGP

ALGCAGGGRIYDFEAAWDAILASSDSSFLNEEYCIVKRLYNSRNSQSNN

IAAYITAHLLPPVAQVFHQSAGSITDLLRGVGNGNDATGLVANAQRYIA

QAASQVHV

FIBL-NT3 Protein Length = 372 MW = 40503.7
pI = 7.39
SEQ ID NO: 2
MHHHHHHAPSVTINQYSDNEIPRDIDDGKASSVISRAWDYVDDTKSIA

ILNVQEILKDMASQGDYASQASAVAQTAGIIAHLSAGIPGDACAAANVI

NSYTDGVRSGNFAGFRQSLGPFFGHVGQNLNLINQLVINPGQLRYSVGP

ALGCAGGGRIYDFEAAWDAILASSDSSFLNEEYCIVKRLYNSRNSQSNN

IAAYITAHLLPPVAQVFHQSAGSITDLLRGVGNGNDATGLVANAQRYIA

QAASQVHVYAEHKSHRGEYSVCDSESLWVTDKSSAIDIRGHQVTVLGEI

KTGNSPVKQYFYETRCKEARPVKNGCRGIDDKHWNSQCKTSQTYVRALT

SENNKLVGWRWIRIDTSCVCALSRKIGRT

FIBL-linker-NT3 Protein Length = 382 MW = 41134.1
pI = 7.39
SEQ ID NO: 3
MHHHHHHAPSVTINQYSDNEIPRDIDDGKASSVISRAWDYVDDTKSIA

ILNVQEILKDMASQGDYASQASAVAQTAGIIAHLSAGIPGDACAAANVI

NSYTDGVRSGNFAGFRQSLGPFFGHVGQNLNLINQLVINPGQLRYSVGP

ALGCAGGGRIYDFEAAWDAILASSDSSFLNEEYCIVKRLYNSRNSQSNN

IAAYITAHLLPPVAQVFHQSAGSITDLLRGVGNGNDATGLVANAQRYIA

QAASQVHVGGGGSGGGGSYAEHKSHRGEYSVCDSESLWVTDKSSAIDIR

GHQVTVLGEIKTGNSPVKQYFYETRCKEARPVKNGCRGIDDKHWNSQCK

TSQTYVRALTSENNKLVGWRWIRIDTSCVCALSRKIGRT

FIBL-(NT3)2 Protein Length = 501 MW = 54739.0
pI = 8.28
SEQ ID NO: 4
MHHHHHHAPSVTINQYSDNEIPRDIDDGKASSVISRAWDYVDDTKSIA

ILNVQEILKDMASQGDYASQASAVAQTAGIIAHLSAGIPGDACAAANVI

NSYTDGVRSGNFAGFRQSLGPFFGHVGQNLNLINQLVINPGQLRYSVGP

ALGCAGGGRIYDFEAAWDAILASSDSSFLNEEYCIVKRLYNSRNSQSNN

IAAYITAHLLPPVAQVFHQSAGSITDLLRGVGNGNDATGLVANAQRYIA

QAASQVHVYAEHKSHRGEYSVCDSESLWVTDKSSAIDIRGHQVTVLGEI

KTGNSPVKQYFYETRCKEARPVKNGCRGIDDKHWNSQCKTSQTYVRALT

SENNKLVGWRWIRIDTSCVCALSRKIGRTGGGGSGGGGSYAEHKSHRGE

-continued

YSVCDSESLWVTDKSSAIDIRGHQVTVLGEIKTGNSPVKQYFYETRCKE

ARPVKNGCRGIDDKHWNSQCKTSQTYVRALTSENNKLVGWRWIRIDTSC

VCALSRKIGRT

2. Expression and purification of the fusion protein: the recombinant expression vector obtained in step 1 is transferred into BL21 *Escherichia coli*, expression is induced at a temperature of 37° C., then ultrasonic crushing is performed, the fusion protein is purified by using Ni-NTA, and identification is performed to obtain the fusion protein.
3. An appropriate amount of mulberry silk is taken and placed into a 0.2% sodium carbonate solution, boiling is kept for 30 minutes, then the mulberry silk is taken out and washed with triple distilled water, and the steps are repeated three times to obtain a silk fibroin fiber, external sericin of which is removed, and the silk fibroin fiber is placed on a super clean bench for drying.
4. The silk fibroin fiber is placed into a 9M lithium thiocyanate hydrate for dissolution, the solution obtained after dissolution is transferred into a dialysis bag (the molecular weight cut off is about 14 kDa), and dialysis is performed for 72 hours by using triple distilled water as a dialyzate to obtain a silk fibroin solution.
5. A silk fibroin fiber web is woven by a braider by using the silk fibroin fiber obtained in step 3.
6. The fusion protein obtained in step 2 is mixed with the silk fibroin solution obtained in step 4 according to a certain ratio to obtain a mixed protein solution, the concentration of the mixed protein solution is configured to be 5%-40%, a mass ratio of the fusion protein to the silk fibroin is 1:99 to 50:50, the silk fibroin fiber web obtained in step 5 is placed in a mold, the mixed protein solution is poured in the mold, and freeze drying is performed at a temperature of −70° C. to form a nerve conduit by means of crosslinking of the silk fibroin, the fusion protein and the silk fibroin fiber web.
7. The nerve conduit is soaked in 60% ethanol to undergo deformation processing for 12 h, then is washed with triple distilled water, and is dried to finally obtain a silk fibroin nerve graft having NT-3 activity.

Figure 1:
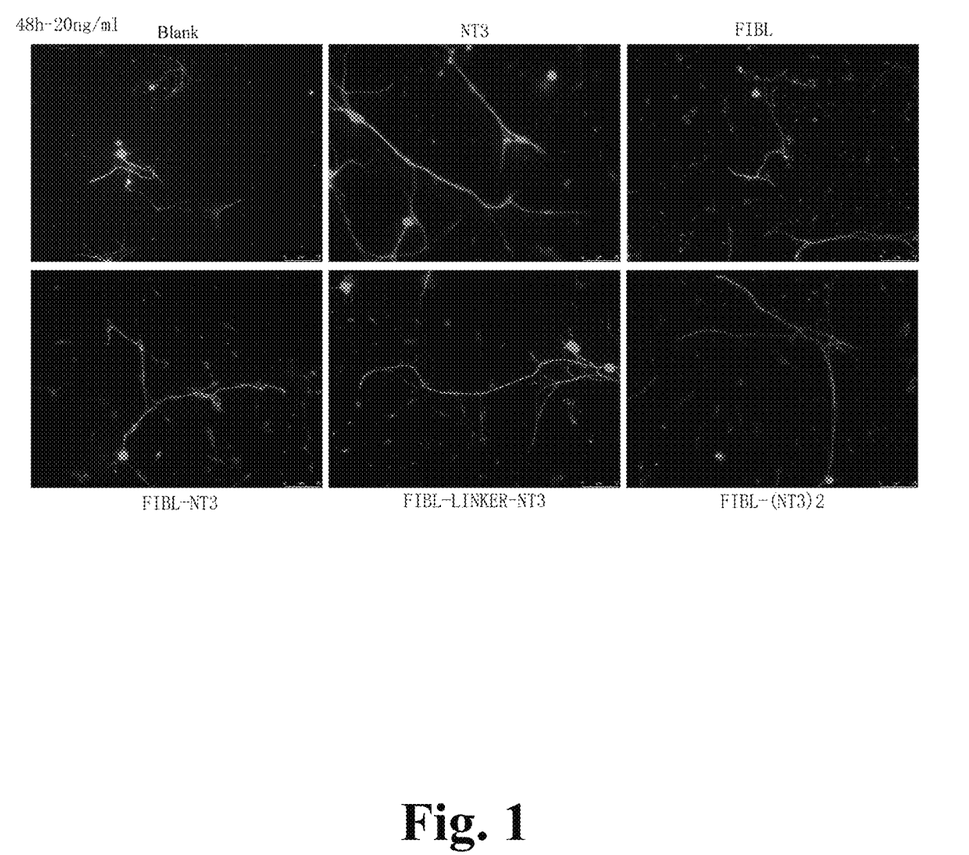
FIG. 1 illustrates effects of NT3-containing fusion proteins of different designs on growth of dorsal root ganglion neurites cultured in vitro.
Figure 2:
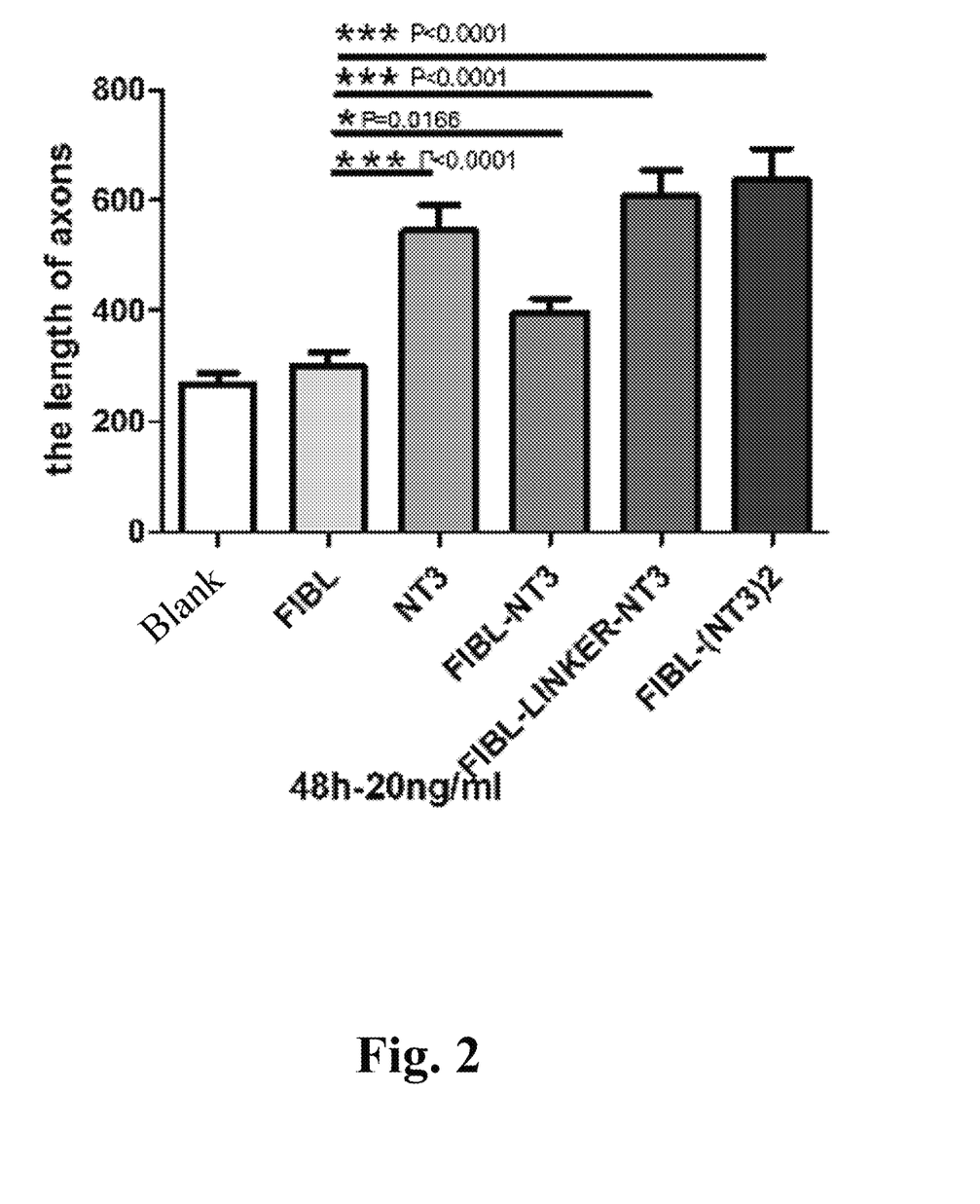
FIG. 2 illustrates effects of NT3-containing fusion proteins of different designs on growth of dorsal root ganglion neurites cultured in vitro.

In a growth plot (FIG. 1) and a statistical graph (FIG. 2) illustrating promotion of silk fibroins fused with NT-3, FIBL, FIBL-NT3, FIBL-linker-NT3, and FIBL-(NT3)$_2$ on DRG axons, data of the statistical graph comes from average values of length counts of 30 neuron axons in each group. It can be seen from the drawings that compared with a blank group, NT3 can promote growth of axons of cells, and FIBL-NT3, FIBL-linker-NT3, and FIBL-(NT3) can more effectively promote the growth of the axons.

What is claimed is:

1. A preparation method for a silk fibroin nerve graft fused with NT3, comprising the following steps:
   synthesizing a gene fragment containing a silk fibroin light chain and NT-3, connecting the fragment to a pET-30 expression vector, and transferring the obtained recombinant expression vector into BL21 *Escherichia coli* to obtain a fusion protein;
   mixing the fusion protein and a silk fibroin solution to obtain a mixed protein solution, placing a silk fibroin fiber web in a mold, pouring the mixed protein solution in the mold, and performing freeze drying to form a nerve conduit; and after deformation processing, finally obtaining a silk fibroin nerve graft having NT-3 activity.

2. The preparation method for a silk fibroin nerve graft fused with NT3 according to claim 1, wherein,
   the silk fibroin fiber web is woven by a braider by using a silk fibroin fiber.

3. The preparation method for a silk fibroin nerve graft fused with NT3 according to claim 1, wherein,
   a preparation method for the silk fibroin solution is: placing a silk fibroin fiber into a lithium thiocyanate hydrate for dissolution, transferring the solution obtained after dissolution into a dialysis bag, and performing dialysis for 60 to 80 hours by using triple distilled water as a dialyzate to obtain the silk fibroin solution.

4. The preparation method for a silk fibroin nerve graft fused with NT3 according to claim 2, wherein,
   a preparation method for the silk fibroin fiber is: placing mulberry silk into a sodium carbonate solution, boiling for 20 minutes or more, taking out the mulberry silk, washing with triple distilled water, and repeating the steps two to four times to obtain the silk fibroin fiber, external sericin of which is removed.

5. The preparation method for a silk fibroin nerve graft fused with NT3 according to claim 1, wherein,
   a concentration of the mixed protein solution is 5% to 40%, and a mass ratio of the fusion protein to the silk fibroin is 1:99 to 50:50.

6. The preparation method for a silk fibroin nerve graft fused with NT3 according to claim 1, wherein,
   the deformation processing is soaking in 60% ethanol for processing for 10 h to 14 h.

7. The preparation method for a silk fibroin nerve graft fused with NT3 according to claim 3, wherein,
   a molecular weight cut off of the dialysis bag is 12-16 kDa.

8. The preparation method for a silk fibroin nerve graft fused with NT3 according to claim 1, wherein, a temperature for freeze drying is −70° C.

9. The preparation method for a silk fibroin nerve graft fused with NT3 according to claim 3, wherein, a concentration of the lithium thiocyanate hydrate is 9 mol/L.

10. A silk fibroin nerve graft fused with NT3, prepared by using the preparation method according to claim 1.

11. The preparation method for a silk fibroin nerve graft fused with NT3 according to claim 3, wherein, a preparation method for the silk fibroin fiber is: placing mulberry silk into a sodium carbonate solution, boiling for 20 minutes or more, taking out the mulberry silk, washing with triple distilled water, and repeating the steps two to four times to obtain the silk fibroin fiber, external sericin of which is removed.

* * * * *